United States Patent [19]
Sielaff, Jr. et al.

[11] Patent Number: 5,514,071
[45] Date of Patent: May 7, 1996

[54] REMOTE INJECTION DEVICE

[76] Inventors: Carl F. Sielaff, Jr., 857 Helston Rd., Bloomfield Hills, Mich. 48304; John F. Trudeau, 39775 Sylvia, Mt. Clemens, Mich. 48045

[21] Appl. No.: 319,316

[22] Filed: Oct. 6, 1994

[51] Int. Cl.⁶ ..................................................... A61M 5/00
[52] U.S. Cl. ........................................................... 600/3
[58] Field of Search ..................... 600/1–8; 128/DIG. 1

[56] References Cited

U.S. PATENT DOCUMENTS

| | | | |
|---|---|---|---|
| 3,596,659 | 8/1971 | Glasser | 128/215 |
| 3,628,523 | 12/1971 | Pirtle, Jr. | 128/2 |
| 3,718,138 | 2/1973 | Alexandrov et al. | 128/214 R |
| 3,820,541 | 6/1974 | Langan | 128/215 |
| 3,880,138 | 4/1975 | Wootten | 128/2 A |
| 3,973,554 | 8/1976 | Tipton | 128/1.1 |
| 3,993,063 | 11/1976 | Larrabee | 128/215 |
| 4,006,736 | 2/1977 | Kranys et al. | 128/2 A |
| 4,250,887 | 2/1981 | Dardik et al. | |
| 4,759,345 | 7/1988 | Mistry | 600/8 |
| 4,846,235 | 7/1989 | Handke | 600/5 |
| 4,897,076 | 1/1990 | Puthawala et al. | 600/8 |

Primary Examiner—Angela D. Sykes
Assistant Examiner—John P. Lacyk
Attorney, Agent, or Firm—Young & Basile

[57] ABSTRACT

An apparatus for remotely administering radioactive material by a syringe into a patient where the syringe is encapsulated in a lead housing. A lever mechanism is operatively attached to a plunger located within the housing via a rod. The lever mechanism activates the plunger against the plunger head of the syringe during the administration of the radioactive material. A specially designed carrier transports the apparatus from the radioactive source to the patient.

18 Claims, 4 Drawing Sheets

REMOTE INJECTION DEVICE

FIELD OF THE INVENTION

The invention relates to an apparatus for administering radioactive material to a patient while protecting an operator from undue exposure to repeated doses of radiation emanating from the radioactive material contained in a syringe.

BACKGROUND OF THE INVENTION

Within recent years, there has been a wide and increasing acceptance of the use of radioisotopes for the diagnosis and treatment of various body malfunctions. As a result of the radioactivity of the radioisotope, considerable hazard is involved to the personnel responsible for injecting the radioisotope within a patient's body. While the dosages applied are themselves not lethal to the patient, constant and repeated contacts with the serums over an extended period of time can create very harmful effects on the medical operators who administer them.

A more recent diagnostic procedure requiring the use of radioisotopes is the clinical use of positron emission tomography (PET). PET has been used for approximately 15 years; and is a non-invasive imaging technique that is used to measure the uptake and distribution of short lived positron emitting radiopharmaceuticals or radiotracers. These radiotracers are generally produced on-site at the hospital in a cyclotron and then injected into the patients prior to imaging. Positron emitting radiotracers are of interest because of their use in transaxial tomography.

Although a variety of positron emitting radiotracers are employed in the study of epilepsy, dementia and cerebral blood flow to mention a few, a widely used radiotracer is fluorodeozyglucose (FDG). FDG is transported from the blood to the brain substance in a manner similar to glucose. FDG is phosphorylated and trapped in the brain substance where there is limited metabolism that allows adequate time for tomographic positron imaging. PET using FDG permits a non-invasive method of quantifying cerebral metabolism in humans and thereby provides a physiological tool that discerns pathologic conditions before morphologic manifestations are discernable. Thereby, the clinical use of PET has increased considerably during the past few years.

Recent studies have indicated that PET exposes the technologist to the largest doses of radiation compared to other modalities. Protection from radiation exposure is achieved primarily by three factors: time, distance, and shielding. Radiation exposure is directly proportional to the amount of time spent in a radiation field. The quicker the operator can remove himself from the radiation field, the less radiation exposure he will experience. Distance provides a second form of protection in that the dose to an individual decreases with the square of the distance from the radiation field. Therefore, if one doubles the distance between an individual and a source of radiation, the radiation exposure to the individual is reduced to one-fourth. Shielding provides the third form of protection. Shielding is of two general types: bench top and syringe shielding. Bench top shields are generally constructed of lead bricks and usually have a viewing and access porthole so that the operator can remove the syringe from its lead casing to be placed within another bench top shield on a transport apparatus. The operator uses the transport apparatus to move the syringe to the patient testing site. Many times the transport apparatus itself is not sealed in all directions allowing more exposure to the operator.

The current invention addresses these forms of protection from radiation exposure by limiting the time that the operator is exposed in the radiation field, by providing a remote injection device and thereby adding distance during the injection procedure, and finally by providing an adequate shielding device during the transport and administration of the radioactive material.

SUMMARY OF THE INVENTION

The present invention provides an apparatus that is designed primarily, but not limited to the injection of PET radiotracers that provides an effective shield for the operator to minimize exposure to positron and high energy photons emitted from the radiotracers.

As done currently, the operator receives the PET radiotracers from the appropriate cyclotron source in an acrylic encased syringe shield and that is further enclosed in a lead tubular container. The syringe shield has been reconfigured to be accommodated within a specially designed lead housing of the present invention. The syringe shield effectively stops the positrons from penetrating the surface of the shield while the operator is transferring the syringe and syringe shield from the lead tubular container into the lead housing of the present invention.

The lead housing is generally rectangular having a lid portion and base portion hingingly attached and designed to provide quick and easy insertion of the syringe shield therein. The internal configuration of the lead housing alleviates the time the radioactive syringe is outside of the lead housing thereby minimizing contamination of the surroundings. The housing is bored such that an annular groove on the shield rests between locating pins extending from the bottom of the interior lead housing. The locating pins further place the syringe holder in alignment so that a needle can be inserted through a small aperture at one end of the housing to the syringe.

Once the shield with the syringe is loaded within the lead housing, the lead housing configuration essentially eliminates radiation exposure by eliminating straight seams between the lid and base portions.

A lead plunger located within the housing is at a distal end from the needle. The lead plunger is connected to a rod that extends external of the lead housing through an aperture. The rod is connected at a distal end to an external actuating device. The actuating device is a lever mechanism that provides a rotatably lever that is hinged to the distal end of the rod so that when the lever is rotated it moves the rod and plunger into contact with the syringe and thereby injecting material to its particular destination point.

Inasmuch as the essentially lead housing is heavy, a special cart is provided having a top planar surface upon which the housing and actuating device are mounted. The cart has a lower rectangular frame from which a rotatable wheel extends adjacent to each corner for movement of the cart over a floor in a stable, upright configuration. The cart has a push handle at the rear of the cart to provide ease in maneuverability and to allow the apparatus to be moved within close proximity to the patient. The cart further provides height adjustment to accommodate various patient positions. The apparatus is mounted to a partially rotatable plate on the cart that allows the injection port of the lead housing to be positioned at varying angles with respect to the cart. This allows the operator to move the apparatus and especially the injection port as close to the patient or suitable inlet junction to the patient as possible.

Other objects, advantages and applications of the present invention will become apparent to those skilled in the art when the following description of the best mode contemplated for practicing the invention is read in conjunction with the accompanying drawings.

BRIEF DESCRIPTION OF THE DRAWINGS

The description herein makes reference to the accompanying drawings wherein like reference numerals refer to like parts throughout the several views, and wherein.

DESCRIPTION OF THE PREFERRED EMBODIMENT

Figure 1:
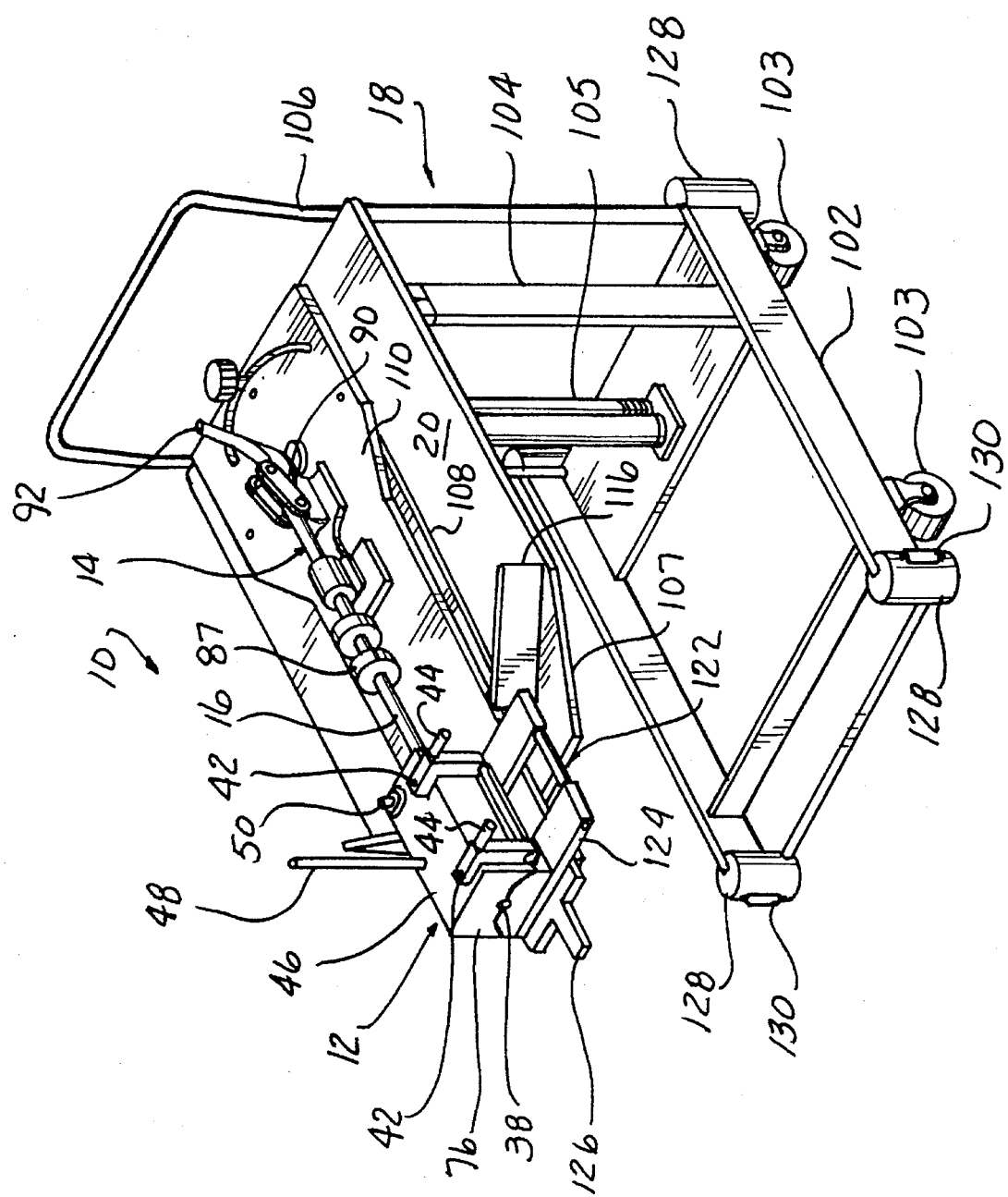
FIG. 1 is a prospective view of the remote injection device located on a specially designed cart.

FIG. 1 shows the remote injection apparatus 10 comprising a lead housing 12 and an actuating means 14 interconnected by rod 16. The apparatus is fixedly mounted to a positioning device comprising a cart 18 in such a manner as to allow the apparatus 10 to pivot in an arcuate manner on the top planar surface 20 of cart 18. The cart 18 is designed to provide a stable transportation means that is easy to maneuver from the load point of the syringe 22 into the lead housing 12 to the point of delivery of the radioactive material at the patient.

Figure 2:
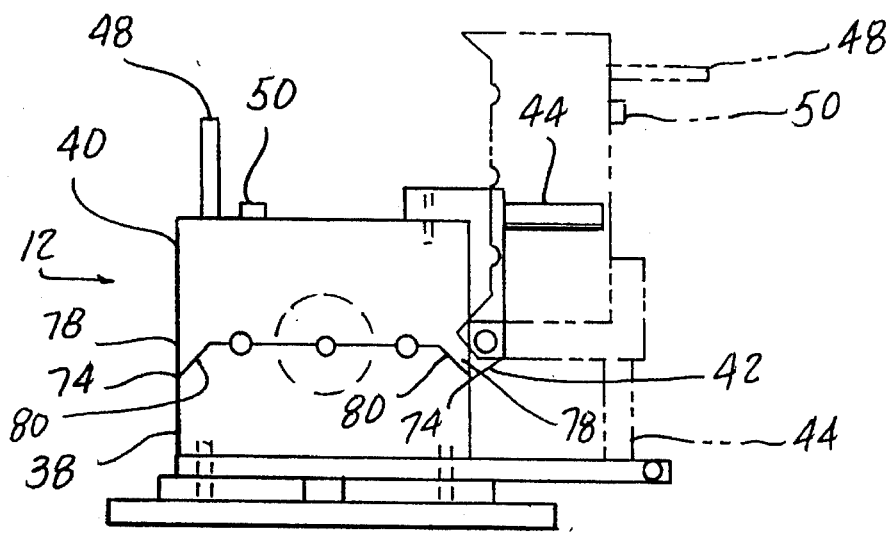
FIG. 2 is a front end view of the remote injection device showing a lead housing having a needle aperture.
Figure 3:
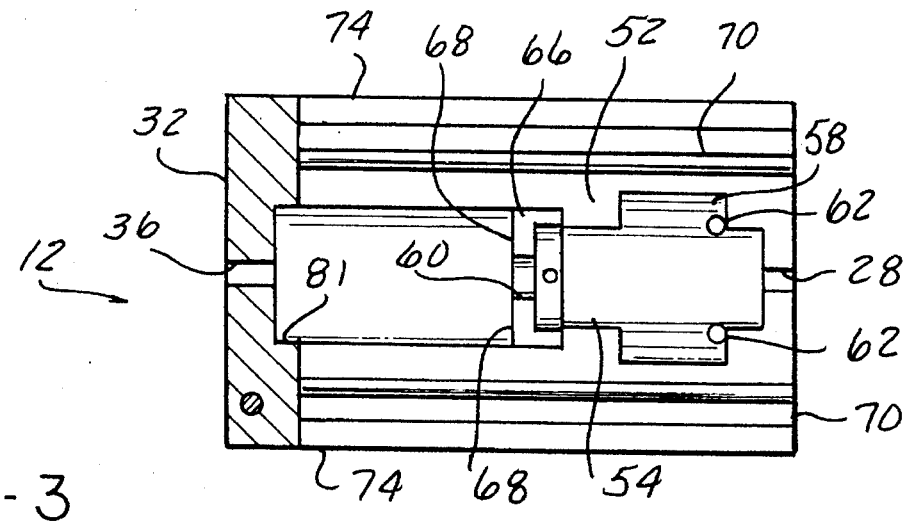
FIG. 3 is a plan view of a base portion of the lead housing with a top portion of the lead housing removed.
Figure 4:
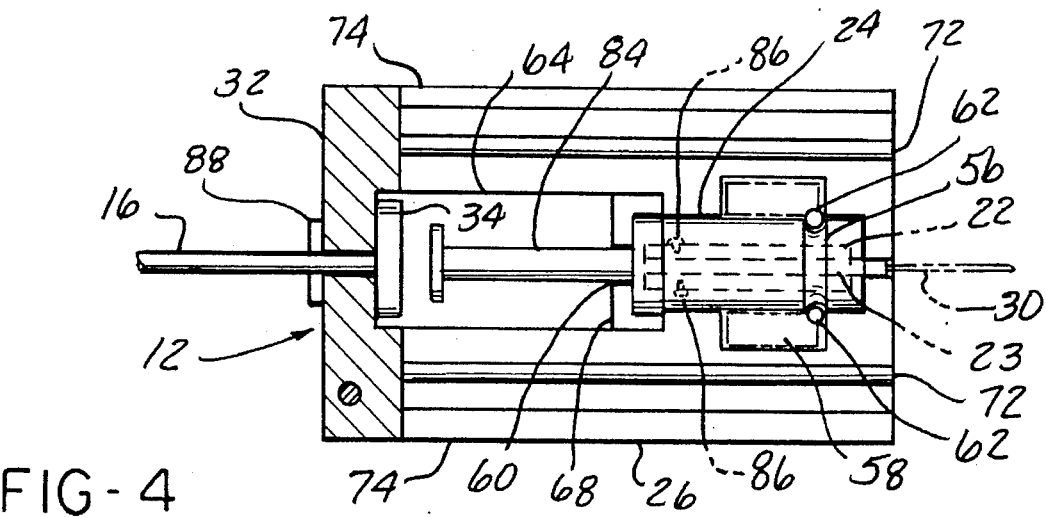
FIG. 4 is the base portion having a syringe enclosed in an acrylic holder positioned in the base and a rod.
Figure 5:
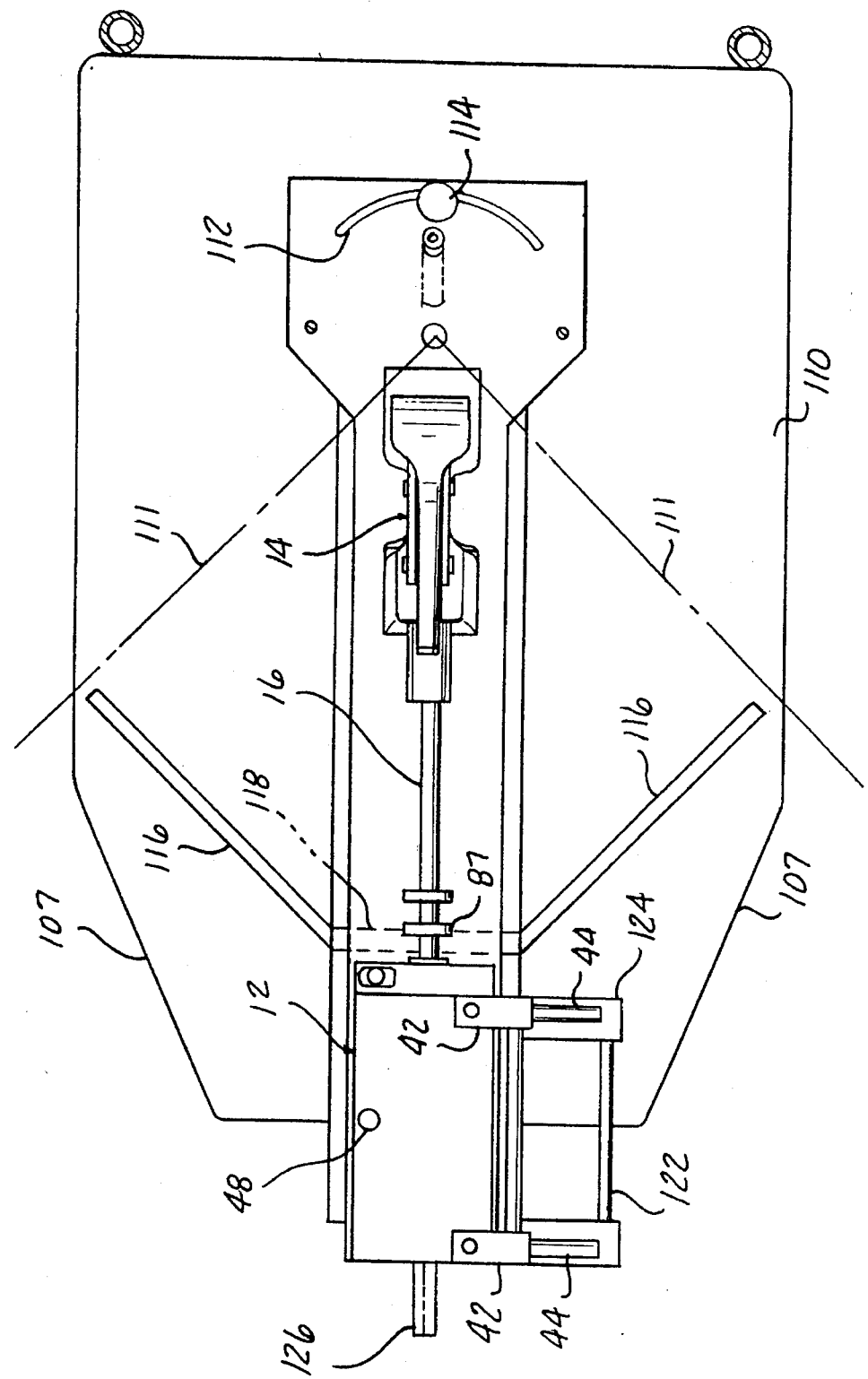
FIG. 5 is a top view of the remote injection device.

Looking at FIGS. 2–4, the rectangular housing 12 is of solid lead material (a high density material) having an inner bore capable of accommodating a syringe 22 having a barrel 23 for containing a quantity of radioactive solution and encased in a protective acrylic, preferably Lucite, shield 24 in a front portion 26 of the housing. A small aperture 28 approximately 0.375 inches in diameter is provided at the front end for installment of a needle 30 at the time of administering the radioactive material to the patient. At a distal end from the needle aperture 28, the housing is provided with a 2.0 inch thick lead back cover 32 which houses a plunger 34 when the apparatus is not activated. Attached to plunger 34 and extending beyond the outside of the back cover 32 out of the housing is a rod 16, which at its distal end is connected to the actuating means 14. An aperture 36 in back cover 32 provides just enough clearance to allow movement of the rod 16 back and forth through the back cover and into the interior of the housing 12. The front portion 26 of the housing comprises a base portion 38 and a lid portion 40 connected by hinging means 42 so that the interior of lead housing 12 can be accessed. A pair of aluminum hinges are bolted on one side of the front portion of the housing to connect the lid and base portions thereof.

On the upper surface 46 of the lid portion 40 is a handle 48 extending vertically from the upper surface. Inasmuch as the lead housing is considerably heavy, the vertical handle 48 provides the necessary torque to open the lid portion 40 and pivot it about its hinging means 42 in an upward position. Each hinge 42 comprises a lateral leg 44 that acts as a support leg when the housing is open (in phantom in FIG. 2). A safety locking knob 50 is fixedly attached to the upper surface 46 near the back cover 32 of the housing 12. The knob 50 provides a manual locking device to prevent the lid 40 from being opened accidentally while maneuvering the apparatus into position.

When the lead housing 12 is in the open position, the operator can quickly and easily deposit a shielded syringe 22 therein and quickly close the housing to alleviate radioactive contamination into the surrounding area. FIG. 3 shows a top view of the base portion 38 of the lead housing with the lid portion 40 removed, thereby exposing the interior 52 of the lead housing. When the operator receives the radioactive-filled syringe 22 from a cyclotron (not shown), it is encased in an acrylic shield 24 that provides moderate protection from radioactivity. The acrylic shield 24 is further encased within a cylindrical lead container (not shown) for the transport from the cyclotron to the receiving pick up area. At that time, the operator removes the acrylic encased syringe from the lead container and quickly deposits the syringe 22 with acrylic shield 24 into the interior 52 of the lead housing. The interior 52 of a housing is configured to provide a foolproof means of insertion of the acrylic shield 24 containing the syringe 22 so that the syringe 22 is in axial alignment with the direction of the needle aperture for administration. An annular bore 54 proximate to the needle aperture 28 is sized in the interior 52 of the lead housing to accommodate the acrylic shield 22. A clearance area 58 positioned on either side of annular bore 54 provides a gripping space for the operator's fingers when depositing and returning the shield. A pair of positioning pins 62 extend from the base portion 38 of the lead housing and fit into appropriately sized apertures (not shown) in the lid portion 40 of the lead housing. These pins 62 are positioned adjacent to each side of an annular groove 56, on the exterior of acrylic shield 24 to hold acrylic shield 24 in place and prevent lateral movement of the shield 24 within the lead housing 12. The annular bore abruptly increases in size at a position away from the needle aperture 28 within the interior 52 of housing 12. This increased annular bore area 64 is sized to accommodate the plunger 34 during its reciprocal movement toward the syringe 22. It should be understood that although only the interior of base portion 38 is shown in FIGS. 3 and 4, the interior of the lid portion 40 is the mirror image of the base 38, in that lid 40 has the other half of the annular bores 54 and 64. The lid portion differs from base 38 in that the lid has apertures sized and positioned to receive positioning pins 62.

A backstop 66 made of a plastic material is set in the enlarged bore area 64 adjacent to annular bore 54. Backstop 66 is generally a U-shaped configuration having upward tabs 68 extending into and traversing a portion of the enlarged bore area 64. An opening 60 is provided between upward tabs 68 for the syringe plunger 84. Backstop 66 retains the syringe 22 in place within annular bore 54 when a needle 30 is being inserted into syringe 22 through needle aperture 28, and prevents the syringe 22 from being pushed into the enlarged bore area 64 by the force of the needle insertion.

Radioactive rays emanate in a straight line from its source. Therefore, it is necessary to provide a structure that houses the syringe that does not provide a straight path along a seam line from which the rays can escape. The current invention provides such a structure.

Along the axial length of the front portion 26 of lead housing 12 on either side of the annular bores 54, 64 is a radial slot 70 extending the length of the front portion. The slots 70 are shaped to accommodate a lead rod 72. The lead rods 72 provide a barrier at the axial seam lines 74 where the lid portion 40 meets the base portion 38 of the housing to prevent radioactive rays to escape laterally from the housing. The rods 72 are fixedly secured to base portion 38 of the lead housing 12 by conventional means such as an adhesive. FIG. 2 shows the front end 76 of lead housing 12 showing the needle aperture 28 therein. It is evident from FIG. 2 that a straight line seam has been avoided between the lid portion 40 and base portion 38 in that the lid portion 40 has an angular ledge 78 running axially along the lateral edge on either side of lead rods 72 to meet and correspond to an angular cutout 80 of the base portion. Therefore, radioactive material cannot escape through a seam line 74 between the container lid 40 and the base 38. A similar angled or tapered seam can also be provided along the front end of lead housing 12 (at the end having needle aperture 28) so that radioactive rays do not have a straight exit path through the seam in the front end. The back end of housing 12 (distal from needle aperture 28) is sealed from radioactive rays by the lead back cover 32.

The syringe 22 encased in the acrylic shield 24 is shown in base 38 in FIG. 4. The annular groove 56 on shield 24 sets adjacent and between positioning pins 62. The back 82 of shield 24 is adjacent to tabs 68 of backstop 66. A small clearance is provided therebetween. The syringe plunger 84 extends through opening 60 and past tabs 68 into the expanded bore area 64. When the operator initially places the syringe and shield in base 38, the syringe 22 has a protective shield (not shown) extending from the syringe in place of the needle 30. When the patient is ready, the protective shield is removed and a needle 30 is installed. The acrylic shield 24 is adjustable to accept various size syringes 22 by means of spring bias screws 86 that can be tightened or loosened to firmly hold any size syringe 22 in place.

Figure 6:
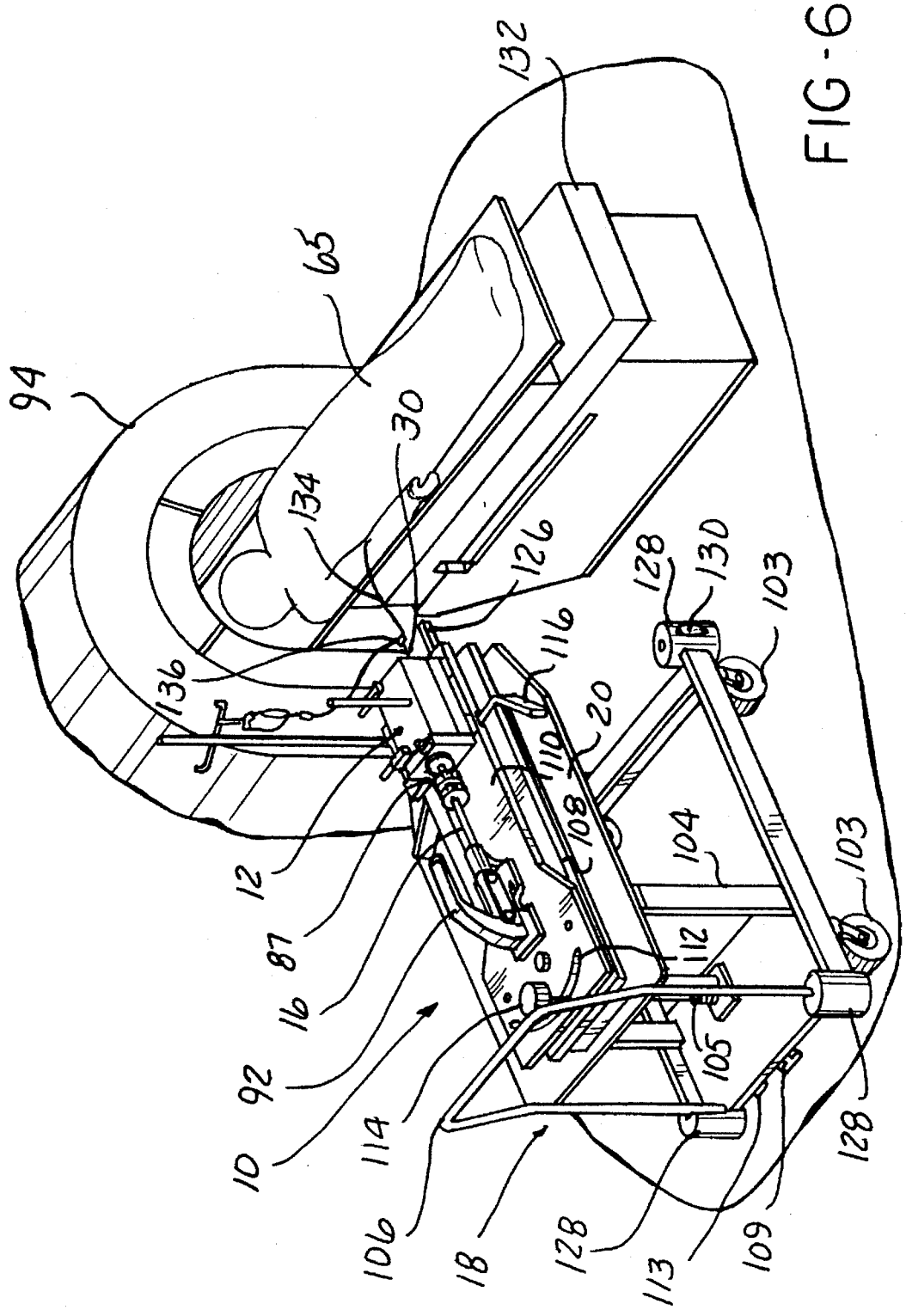
FIG. 6 is a prospective view of the remote injection device being used at the site of a patient located in a PET scanner.

The lead housing 12 is attached to a remote actuating system 14. The actuating system 14 is a lever mechanism that moves plunger 34 into contact with syringe plunger 84. Rod 16 is fixedly attached to the lead plunger 34 located within a cavity 81 in the back cover 32 of the housing at one end, and at a distal end is attached to the lever mechanism 14. Cavity 81 is in axial alignment with syringe plunger 84 and sized to accommodate lead plunger 34 for movement. The rod 16 allows reciprocal movement of the lead plunger 34 within the enlarged bore area 64 of the lead housing. Rod 16 has positionable stops 87 that can be moved along rod 16 to adjust the length of rod 16 that enters into the lead housing 12. This allows the travel distance of plunger 34 to accommodate various syringe 22 sizes. As lead plunger 34 moves toward the syringe plunger 84 and comes into contact with such, the syringe plunger 84 is forced toward the needle aperture 28 such that the radioactive contents within syringe 22 are injected into the appropriate junction whether directly into the patient 65 or through an intervenous junction 136 (FIG. 6). A brass fitting 88 is secured to the outside surface of the back cover 32. The brass fitting 88 maintains linear axial movement of the rod 16 and prevents deviation of rod 16 in any other direction.

The lever mechanism 14 of the preferred invention is configured so that the rod 16 is threadably secured to one end of a bracket 90. The bracket 90 is threadably secured to a lever handle 92. When the lever handle 92 is faced upward and away from the lead housing 12 (as shown in FIG. 1), the rod 16 is in its retracted position wherein lead plunger 34 is located within the cavity 81 of back cover 32. By moving the handle toward housing 12, the bracket 90 pivots forcing rod 16 toward housing 12 and activating the lead plunger 34 in reciprocal fashion into the enlarged bore area 64 of the housing toward the syringe plunger 84 (FIG. 6).

Although it is envisioned that the lead housing 12 and lever mechanism 14 can be fixedly mounted to a stationary surface, the current procedure used in most hospitals requires that the syringe 22 is received from the cyclotron at one destination point and then transferred to the patient 65 already placed inside a scanner 94 at a remote destination point. Therefore, because of the weight of the housing and lever mechanism, a carrying device was designed specifically for the housing 12 and lever mechanism 14 to provide ease in safely maneuvering the apparatus from one location to another and means to gain access to a temporarily immobile patient 65. The carrying device is essentially a cart 18 having an upper planar surface 20 and a bottom frame 102 connected by vertical posts 104. The cart 18 has four swivel wheels 103 extending from the four corners of the frame 102 for transport across the floor. At the back of the cart 18, defined as the end distal to the needle aperture 28, is a handle rail 106 for pushing and positioning the cart 18 to its desired location. A positioning brake 113 is provided to lock the back wheels of cart 18 once the cart is at its desired location. The positioning brake 113 is foot operated. The cart 18 also provides height adjustment means 105 to lower or raise the lead housing 12 to a desired height. The preferred embodiment utilizes conventional hydraulic means to adjust the height of the upper planar surface 20 having a foot pedal actuating means 109. It is foreseeable that an unusually high height dimension may be required. To maximize stability of cart 18 for such requirements, counterweights may be added at bottom frame 102 to maintain a safe center of gravity.

The upper planar surface 20 has forward corners 107 cut to form a hexagonal shaped surface. An aluminum plate 108 is fixedly attached to the center area of the upper planar surface 18 along the axial length of the cart 18. A second plate or top plate 110, preferably aluminum or steel, is attached for pivotal movement on the first plate 108. The lead housing 12 mounted on a small plate 124 and the lever mechanism 14 is fixedly secured to the top surface of the second plate 110 so that lever mechanism 14 is proximate to the cart handle rail 106 and the needle aperture 28 is at a distal end. An arcuate slot 112 on the top plate 110 having a lock knob 114 confines the pivotal movement of the top plate 110 to a 90° rotation wherein the top plate 110 can move 45° in each direction from its center point to the direction as shown by lines 111. Once the top plate 110 has been positioned in its desired angle, the top plate 110 can be locked in place by fictionally securing the top plate 110 to the bottom plate 108 by means of the lock knob 114. To provide support for the top plate 110 at its angled position, an aluminum support block 116 is angularly secured on each side of the bottom plate 108 on cart 18. An acetal resin such as Delrin is secured to the top of each support block 116 to provide a frictionless surface upon which top plate 110 pivots. A band of Delrin is also applied to a portion 118 of the bottom plate for the same purpose. To facilitate pivotal movement of housing 12, a side handle 122 extending from plate 124 is used to push and pull the lead housing 12.

In order to maneuver the remote injection apparatus as close to the patient as possible, the top plate 110 is extended beyond the forward end of the cart 18. A center nose 126 extends from beyond the forward surface of the top plate 110. The center nose 126 protects the needle 30 and needle protection (not shown) during the maneuvering of the cart 18 into position at the patient 65. The extension of the top plate 110 beyond the upper planar surface 20 of cart 18 and angled corners 107 of upper planar surface 20 provide closer positioning maneuverability of the apparatus 10 to the patient 65.

To further protect the remote injection apparatus 10 from damage and to provide a more frictionless surface when in contact with immovable objects, the cart 18 is provided with nylon bumper guards 128 adjacent the swivel wheels 103. The front bumper guards 128 have integral nylon rollers 130 that extend slightly beyond the bumper guard 128. The rollers 130 provide added cushioning attributes to cart 18. It is clear to see that cart 18 is structured to provide a stable and safe transport means for the remote injection device 10.

In operation, the operator will open the top section 40 of the lead housing 12 via handle 48 making it ready for entry of the syringe 22. In the open position, the hinge leg extension 44 rests against the plate 124 to provide a support of the lid section 40. The operator will receive the syringe 22 from the cyclotron exit port and will remove the acrylic encased syringe from a lead tubular container (not shown). Quickly the operator will place the acrylic shield 24 into the interior of the lead housing 12 so that the annular groove 56 of the acrylic shield 24 rests between the positioning pins 62 in the interior of the housing so that the positioning pins 62 are received in the annular grooves 56 of the shield 24. The syringe plunger 84 will extend beyond the backstop 66 through opening 60 into the enlarged annular area 64 and the acrylic holder 24 will be positioned proximate to backstop 66. The operator will then close the lid portion 40 of the lead housing 12 to minimize further contamination through radiation. At this time, virtually all radiation contamination is eliminated. Lead rods 72 and the ledges 78 formed along the axial length of housing 12 prevent radiation to escape the sides of housing 12. The thick back plate 32 prevents radiation to escape the back of housing 12. The only access port for the radiation is the needle aperture 28 which is approximately 0.375 inches diameter. The needle aperture 28 can be made smaller, if desired, since the size is only limited by the machining process. During testing of this remote injection apparatus at a hospital, the study indicated that the apparatus 10 provided 99.7% protection from radiation contamination.

After the syringe 22 is inserted into the housing, the apparatus 10 is transported to the patient 65 who is already laying on a gantry 132 at the scanner 94 as shown in FIG. 6. In many procedures, a saline solution will be administered intravenously to the patient 65 through an IV 134. The operator can position the remote injection apparatus 10 proximate to the patient 65 at the desired height and distance. Once a check of the IV solution and patient is taken, the radioactive material can be administered. The needle protection can be removed and replaced with needle 30. The IV junction 136 can be placed close to the needle 30 so that the needle 30 impales the junction 136. As the operator moves the lever handle 92 toward lead housing 12, rod 16 and plunger 34 move forward toward the syringe 22 to activate the syringe plunger 84 to expel the radioactive material to administer the material through the IV 134 to the patient 65. As an alternate procedure, the needle 30 can be directly injected into patient 65.

With this invention, the operator is protected from radioactive contamination throughout most of the procedure. The operator limits his radiation exposure by all three factors. Time of exposure is limited by enclosing the radioactive material soon after it is received from the cyclotron. The distance from the radioactive material is increased by the remote lever mechanism 14 distal from the injection port 28 during the injection process. The shielding from the radioactive material is increased by providing a housing that surrounds the material in approximately two inches of solid lead.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. An apparatus for remote injection of radioactive solution into a patient, said apparatus adapted to hold a syringe having a needle, syringe plunger and a barrel for containing a quantity of the radioactive solution wherein said radioactive solution emits radioactive rays therefrom, said apparatus comprising:

a cylindrical shield constructed of radiation attenuating material for enclosing the syringe;

a housing comprising a first portion and second portion hingedly attached thereto and opening to an inner bore disposed in said housing for encapsulating the syringe shield, said housing having a needle aperture at one end of said housing adapted for insertion of the needle into the syringe and projecting therefrom;

said housing comprising a reciprocating plunger within the inner bore of the housing;

an actuating means for selectively moving the plunger in axial movement against the syringe plunger to cause penetration by the needle; and connecting means for securing the actuating means in axial alignment to the plunger disposed in the housing.

2. The apparatus of claim 1, wherein the housing is essentially rectangular and constructed of high density material, said housing having a pair of lateral sides extending the axial length of the housing, wherein the first portion of the housing has an angular ledge extending along each lateral side of the housing, and the second portion of the housing has a corresponding angular cut out extending along each lateral side of the housing wherein when the first portion and second portion of the housing are in a closed position and forming a seam around the periphery of the housing, radioactive rays do not escape the seam of the housing.

3. The apparatus of claim 1, wherein the housing further comprises at least one lead rod extending the axial length of the housing and fixedly attached to the second portion adjacent the inner bore.

4. The apparatus of claim 3 wherein the cylindrical shield has a annular groove proximate one end of the shield and the housing has a pair of vertical pins traversing the inner bore wherein the annular groove is adapted to receive the pins for positioning the cylindrical shield in the inner bore of the housing.

5. The apparatus of claim 4 wherein the housing further comprises a backstop located in the inner bore wherein the cylindrical shield is disposed in the inner bore between the backstop and needle aperture.

6. The apparatus of claim 1 wherein the hinging means of the housing comprises extending legs for support when the housing is in the open position.

7. The apparatus of claim 5, wherein the housing further comprises a back plate having a cavity for housing the plunger.

8. The apparatus of claim 7, wherein the connecting means is a rod connected at one end to the plunger through an aperture in the back plate and connected at a distal end to the actuating means.

9. The apparatus of claim 8, wherein the actuating means is a lever mechanism having a lever handle operatively connected to said rod.

10. The apparatus of claim 9 wherein the apparatus further comprises positioning means for aligning the housing such that the needle is proximate to a predetermined point of penetration.

11. The apparatus of claim 10, wherein the positioning means comprises a rotatable surface, said housing and actuating means fixedly attached to the rotatable surface.

12. The apparatus of claim 11, wherein the positioning means further comprises a cart having a planar surface, said rotatable surface attached thereon.

13. The apparatus of claim 12, wherein the rotatable surface comprises a top plate for fixedly attaching housing and actuating means thereon, said rotatable surface having a forward end extending beyond a front end of the planar surface of the cart.

14. The apparatus of claim 13, wherein the forward end has a needle guard integral therewith and extending beyond said front end of the planar surface of cart to protect said needle.

15. The apparatus of claim 14, wherein said cart has height adjustment means for raising and lowering the planar surface.

16. The apparatus of claim 15, wherein the cart has wheels extending from the lower frame supporting the cart for movement over a floor in a stable upright configuration.

17. An apparatus for remote injection of radioactive solution into a patient, said apparatus adapted to hold a syringe having a needle, syringe plunger and a barrel for containing a quantity of the radioactive solution, wherein said radioactive solution emits radioactive rays therefrom, said apparatus comprising:

a shielding means for enclosing said syringe, said shielding means constructed of radiation attenuating material;

a means for encapsulating the syringe and shielding means, wherein the encapsulating means virtually eliminates radioactive rays from escaping;

a means for transporting the syringe and encapsulating means to a patient;

a means for inserting the needle to the syringe through the encapsulating means;

a means for positioning the needle to a predetermined point of penetration;

a means for remotely actuating the syringe to cause penetration by the needle and inject the quantity of radioactive solution to the point of penetration.

18. A method of remotely injecting radioactive solution into a patient wherein said radioactive solution emits radioactive rays therefrom, comprising the steps of:

shielding syringe in a radiation attenuating material, said syringe having a barrel for containing a quantity of radioactive solution therein;

encapsulating the syringe, wherein the encapsulating means virtually eliminates radioactive rays from escaping;

transporting the syringe and encapsulating means to a patient;

inserting a needle to the syringe through the encapsulating means;

positioning the needle to a predetermined point of penetration; and remotely actuating the syringe to cause penetration by the needle for injecting the quantity of radioactive solution to the point of penetration.

* * * * *